(12) United States Patent
Chowdhury

(10) Patent No.: US 10,092,224 B2
(45) Date of Patent: Oct. 9, 2018

(54) CUMULATIVE MEASUREMENT OF AN ANALYTE

(71) Applicant: Dermal Diagnostics Limited, Loughborough (GB)

(72) Inventor: Dewan Fazlul Hoque Chowdhury, Loughborough (GB)

(73) Assignee: DERMAL DIAGNOSTICS LIMITED, Loughborough (GB)

( * ) Notice: Subject to any disclaimer, the term of this patent is extended or adjusted under 35 U.S.C. 154(b) by 750 days.

(21) Appl. No.: 14/403,098

(22) PCT Filed: May 21, 2013

(86) PCT No.: PCT/GB2013/051322
§ 371 (c)(1),
(2) Date: Nov. 21, 2014

(87) PCT Pub. No.: WO2013/175196
PCT Pub. Date: Nov. 28, 2013

(65) Prior Publication Data
US 2015/0173659 A1     Jun. 25, 2015

(30) Foreign Application Priority Data
May 21, 2012   (GB) .................... 1208950.4

(51) Int. Cl.
*G01N 33/49* (2006.01)
*A61B 5/145* (2006.01)
*A61B 5/15* (2006.01)

(52) U.S. Cl.
CPC ...... *A61B 5/14532* (2013.01); *A61B 5/14514* (2013.01); *A61B 5/150022* (2013.01); *A61B 5/150091* (2013.01); *A61B 5/150984* (2013.01); *G01N 33/49* (2013.01); *F04C 2270/041* (2013.01)

(58) Field of Classification Search
None
See application file for complete search history.

(56) References Cited

U.S. PATENT DOCUMENTS

2001/0016682 A1   8/2001   Berner et al.
2003/0175806 A1   9/2003   Rule et al.

FOREIGN PATENT DOCUMENTS

| CN | 1129898 | 8/1996 |
|---|---|---|
| WO | WO 95/01128 | 1/1995 |
| WO | WO 2012/001365 | 1/2012 |

OTHER PUBLICATIONS

European Patent Office International Search Report and Written Opinion dated Aug. 21, 2013, for PCT/GB2013/051322 filed May 21, 2013, Applicant, Dermal Diagnostics Limited (3 pages).

*Primary Examiner* — Larry D Riggs, II
(74) *Attorney, Agent, or Firm* — McCracken & Gillen LLC

(57) ABSTRACT

A method of monitoring the level of an analyte such as glucose in a subject comprises repeated steps of extracting a quantity of the analyte from the subject into a sample, for example using reverse iontophoresis, then measuring the concentration of the analyte with a method that depletes the analyte. Whereas known methods aim to deplete the analyte fully between extraction steps, the present method allows the concentration to build up with each cycle and measures successive changes in concentration. The higher concentrations present permit more reliable measurements to be made. The sample may be primed with an initial quantity of the analyte.

15 Claims, 2 Drawing Sheets

CUMULATIVE MEASUREMENT OF AN ANALYTE

TECHNICAL FIELD

The invention relates to methods and devices for monitoring the level of an analyte in a subject, for example to measure changes in the level of glucose in the blood or interstitial fluid of a patient over a period of time. It has particular utility when concentrations of the analyte that can be extracted from the subject are low, which is typically the case when reverse iontophoresis is used as the method of extraction.

BACKGROUND OF THE INVENTION

Continuous glucose monitoring devices use the technique of reverse iontophoresis to extract the glucose analyte from the interstitial fluid of a patient for the purpose of measuring changes in glucose levels. Such devices take the form of a patch held in intimate contact with the skin of a patient and comprise a sensing chamber containing electrochemical sensors which are arranged to form part of an electrical circuit. The chamber is filled with a fluid medium or a gel through which the analyte can diffuse or be transported from the skin to the sensors. Either the medium or a surface of the sensors is impregnated with an enzyme that reacts with the analyte to convert it into a different form (gluconic acid in the case of a glucose analyte) and to produce electrons in the process. The electrons can flow around the circuit to create a current, the magnitude of which corresponds to the concentration of the analyte in the medium surrounding the sensor. However, the magnitude of the current is typically only tens or hundreds of nanoamps so it is a challenge to measure it accurately and to distinguish the current signal from background electrical noise. In addition, the sensors may not operate in a reliable, linear manner at low concentrations of the analyte in the sample.

Known devices are operated to carry out an initial period of reverse iontophoresis for analyte extraction, followed by a period of sensing which is often 2 to 3 times longer than the extraction period, so as to ensure all the analyte that has been extracted from the subject during the preceding period has time to react with the sensors. One glucose monitoring device that was commercially available under the trade mark Glucowatch operated with an iontophoresis period of 3 minutes followed by a sensing period of 4 to 5 minutes. The cycle is repeated at intervals, each time a new reading of the subject's glucose level is required, and on each occasion the sensing period is long enough to deplete substantially all of the extracted glucose in the sample.

SUMMARY OF THE INVENTION

The invention provides a method of monitoring the level of an analyte in a subject, comprising the steps of:
(a) measuring the concentration of the analyte in a sample;
(b) introducing into the sample a quantity of the analyte that is representative of the level of analyte in the subject;
(c) re-measuring the concentration of the analyte in the sample;
(d) determining the level of the analyte in the subject based on the difference between the measurement of concentration in step (c) and the previous measurement of concentration; and
(e) repeating steps (b) to (d) at intervals to generate a sequence of determinations over time.

This invention differs from the prior art in that the method does not depend on measuring the absolute value of the concentration of analyte in the sample but on the difference between concentrations after successive intervals of extraction from the subject. Thus the concentration of analyte in the sample can be allowed to build up over successive intervals and the magnitude of the signal from the sensors increases accordingly, permitting more precise and accurate measurement.

In the case where the process used to measure the concentration of analyte in the sample depletes the analyte in the sample, the measurement in step (c) may be controlled such that each measurement depletes only a small proportion of the analyte, to ensure that the concentration of analyte in the sample increases over successive intervals. If necessary, the determination of the analyte level in step (d) may employ an algorithm that makes allowance for the depletion of analyte due to the measurement process. The determination step may also make allowance for depletion of analyte during the intervals between successive measurements. Alternatively, if there is a rest period between each measurement step (c) and the succeeding introduction step (b), then the method may comprising a further step of taking an interim measurement of the concentration of the analyte in the sample after rest period, immediately before each introduction step (b), that interim measurement to be used as the previous measurement of concentration in the determination step (d).

A preferred variant of the method according to the invention includes an initial step of introducing into the sample a quantity of the analyte prior to the first measurement step (a), preferably from a source other than the subject. The initial quantity of the analyte ensures that even in the first measurement step, the concentration of analyte is sufficient for an accurate measurement to be made.

Reverse iontophoresis is a preferred technique for the step (b) of introducing into the sample a quantity of the analyte that is representative of the level of analyte in the subject. However, other techniques could be used, for example simply adding a drop of blood or other fluid into the sample (with due allowance being made when measuring the concentration of analyte for any resulting change in the volume of the sample).

The analyte is preferably glucose but other molecules, ions or particles are possible targets, for example lactate, urea, potassium, phenylalanine, prostaglandin E2 and drugs including but not limited to phenytoin, caffeine, theophylline and lithium.

If the determined level of analyte deviates from a predetermined range of acceptable values, a warning signal may be generated.

DRAWINGS

DETAILED DESCRIPTION OF THE INVENTION

Figure 1:
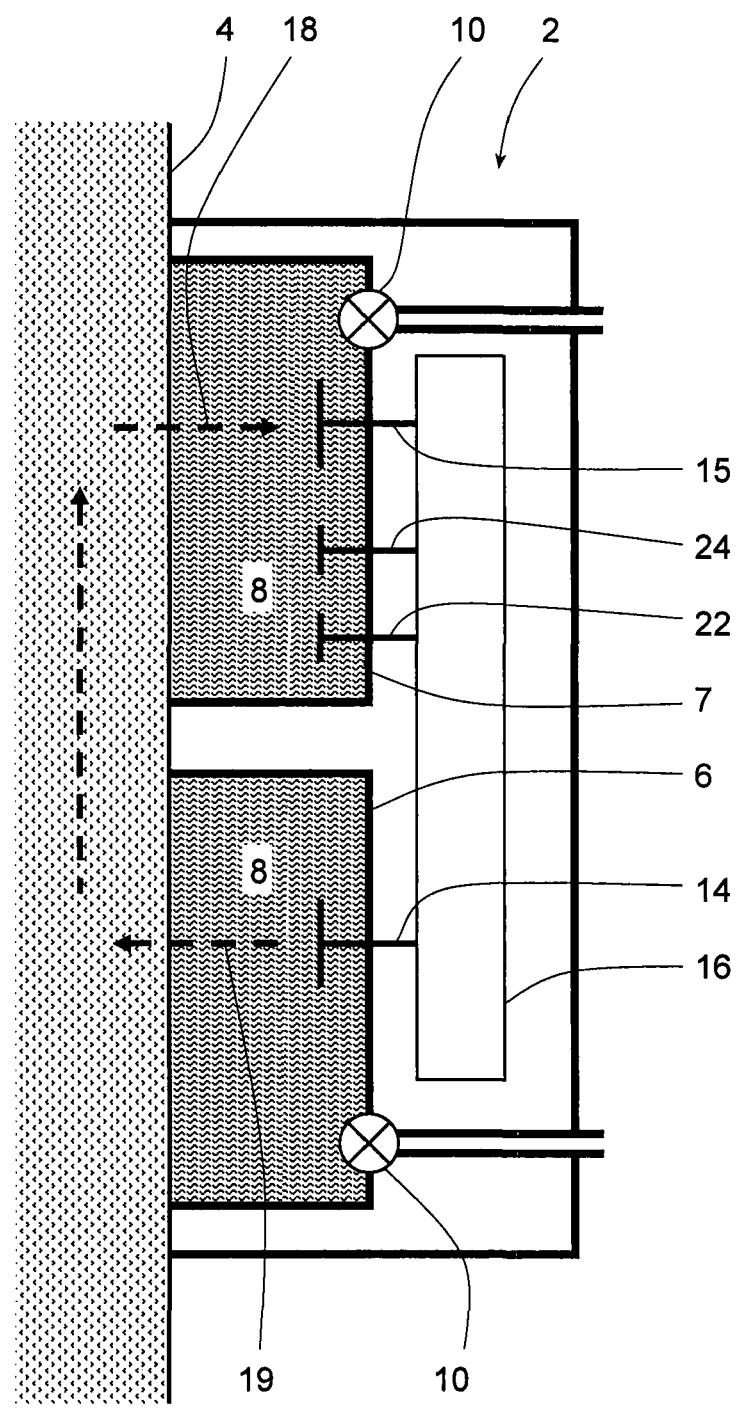
FIG. 1 is a schematic cross section through a reverse iontophoresis patch in which the present invention may be performed.

FIG. 1 (not to scale) schematically shows part of a reverse iontophoresis patch 2, which is applied to the surface of the skin 4 of a subject. The patch 2 may be held against the skin 4 by any means, for example by an adhesive layer (not shown) that forms part of the patch 2 or by being clamped by an elasticated band or some other suitable mechanical restraint means. The patch includes an anode chamber 6 and a cathode chamber 7, each containing a conductive liquid or other medium 8 that is in contact with the surface of the skin 4, either directly or through a permeable membrane (not shown). In the case where the conductive medium is stored as a liquid prior to use, the chambers 6,7 may be provided with inlet ports 10, through which the liquid 8 can delivered from a source outside the patch 2. Once the liquid has entered the chamber it may remain as a liquid conductive medium or may react to form a viscous gel-like medium, where necessary by reacting with a suitable agent, in dry or semi solid form, such as a viscosity enhancing agent or cross-linking agent that is pre-stored within the anodal and/or cathodal chamber; this method would enhance the stability of the sensors by preventing contact of liquid with the sensor surface on storage. In the case of enzyme based sensors for example, the enzyme is susceptible to being degraded when in contact with liquids over prolonged periods.

The respective chambers 6,7 contain a pair of working electrodes, namely an anode 14 and a cathode 15, each of which is immersed in the liquid 8. During operation of the device to perform reverse iontophoresis, the working electrodes 14,15 are controlled by microelectronic circuitry 16 within the patch 2 to induce a flow of ions 18 from the skin 4 of the subject towards the cathode 15 and a balancing flow of ions 19 into the skin 4 from the anode 14. The flow of ions 18 out of the skin 4 transports analytes from the interstitial fluid of the subject into the liquid 8 in the cathode chamber 7, where they disperse and become available for detection by the sensors 22,24. The sensor 22 may be a sensor electrode that is provided with a coating that reacts electrochemically with a target analyte in the liquid 8, e.g. glucose, to generate a measurable current from the electrode 22 that indicates the rate of reaction and hence the concentration of the target analyte in the liquid 8. A similar sensor electrode 24 may be used to measure the concentration of a different analyte in a similar manner. Each of the sensor electrodes 22,24 may require a corresponding counter-electrode (not shown) in contact with the liquid 8 to complete an electrical circuit. The counter-electrode may be a dedicated electrode or may be one of the working electrodes 14,15 as known in the art. The sensor for detecting and measuring the test species and analyte may be substituted with suitable alternatives widely established as current state of the art, including fluorescent sensors, ion selective electrode type sensors, DNA/RNA based sensors and antibody based sensors.

The purpose of the patch 2 is to give a measure of the concentration of the target analyte in the interstitial fluid of the subject. The patch 2 is operated to perform reverse iontophoresis for a given period of time. During reverse iontophoresis, the rate of withdrawal of analytes from the skin 4 is dictated primarily by the current intensity that is flowing through the skin and by the concentration of the analytes within the skin. For a given design of patch the current intensity should be substantially constant so, at the end of the operating period, the quantity of analyte that has accumulated in the chamber should be a true reflection of the concentration of analyte in the interstitial fluid of the subject.

We shall now describe a preferred method of operating the device in accordance with the present invention for monitoring blood levels of glucose in a subject. One of the sensor electrodes 22 has the enzyme glucose oxidase immobilised on its surface, which is capable of oxidising glucose present within the sample chamber 7, leading to the production of electrons in the presence of a suitable mediator. The electrons are collected by the sensor electrode 22 to generate a small current, which can be detected by the circuitry 16 to measure the concentration of glucose molecules in the chamber 7.

In an initial stage, the fluid sample in the chamber 7 is primed with a quantity of glucose sufficient for the concentration in the sample to be measured reliably. At low concentrations, the generated current may be difficult to distinguish from background electrical noise in the circuit. Also, although a sensor can be produced with very high sensitivity, i.e. high resolution down to nanoamps or sub-micromolar glucose concentrations, the limit of quantification (the point from which the sensor behaves in a linear manner) is found to be much higher, namely around 5-10 micromols. The initial quantity of glucose used to prime the chamber should be chosen to create at least a threshold concentration in the chamber that is sufficient to overcome these problems. The initial quantity of glucose could be provided from the subject by operating the reverse iontophoresis process for a sufficiently long period but it is preferred that it should be introduced into the chamber from an independent source, optionally at the time of manufacture. Given also that glucose acts as fuel for microbes, it may be preferable to entrain the glucose within the sensor chamber in a form that does not affect the stability of the sensor, such as dry film, powder, particulate, or semi-solid form, instead of incorporating it into the electrolyte. This would dissolve and disperse within the liquid electrolyte that is transported to the sensor chamber immediately prior to use of the patch and device. An initial measurement of the glucose concentration in the chamber 7 is then made.

Next, the working electrodes 14,15 of the device are operated to carry out reverse iontophoresis for a period of time necessary to extract a measurable quantity of glucose from the subject and deliver it to the sample chamber 7. This may be a shorter period than in the prior art because the quantity of glucose extracted does not have to reach the threshold level for reliable measurement, which has already been achieved by the initial priming of the sample. The quantity extracted only has to be sufficient to allow a difference in concentration in the sample to be detected, as described below. The extraction period may range from 2 to 15 minutes.

Immediately following the extraction period, the sensor electrode 22 is operated to take a "point" measurement of the glucose concentration in the sample chamber 7.

Operation of the electrode involves oxidation of glucose to gluconic acid, thus depleting the concentration of measureable glucose in the chamber. Whereas in the prior art the aim was to measure and thus deplete all of the glucose in the chamber, in accordance with the present invention it is desired to minimize such depletion, in order that the concentration of glucose should build up over successive intervals of operation. Thus the measurement step should be carried out for as short a time as possible, sufficient to determine an accurate concentration value, for example 1 or 2 minutes. In one example, 10 readings are taken over 120 seconds, and peak current is averaged over a stable region to give the current readout for that particular time point.

Typically a delay then follows before a further cycle of extraction and then measurement is carried out, depending on the frequency of measurements that is required for the subject in question.

Figure 2:
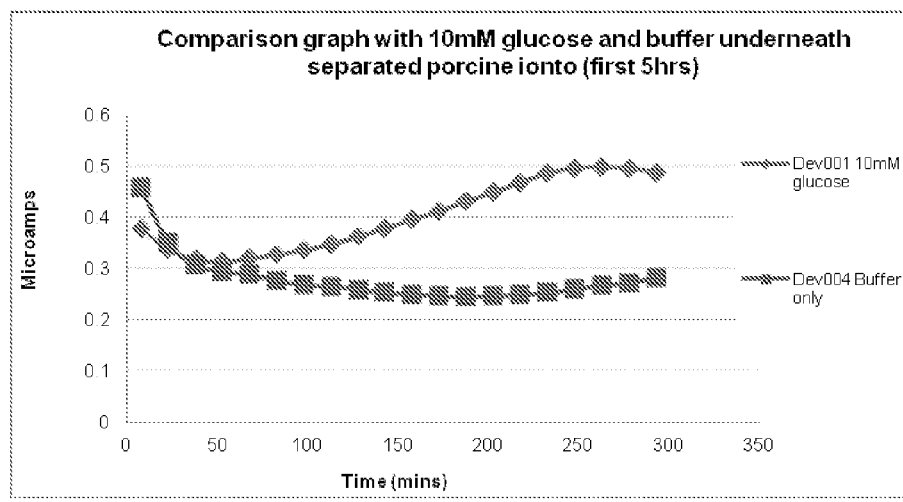
FIG. 2 is a plot of current measurements against time from a glucose sensor placed in contact with (a) glucose extracted cumulatively from porcine skin and (b) a buffer solution.

The method of operating the device according to the invention does not deplete the entire glucose concentration in the sample chamber, therefore the glucose level builds up over time and a cumulative glucose profile is recorded as shown in FIG. 2. The plot labelled Dev001 shows the current signals measured from the cumulative extraction of glucose over a period of 5 hours using porcine skin bathed in a 10 mM solution of glucose. The skin was subjected to reverse iontophoresis at a current density of 0.3 mA cm$^{-2}$ for 5 minutes, the sensor was then switched on for 2 minutes and readings taken periodically during that time. The sensor readings from a stable plateau region were averaged to derive the plotted value. This was followed by a rest period of 8 minutes before the cycle was repeated, over a total period of 5 hours in this case. The plot labelled Dev004 represents a control sample of porcine skin bathed in buffer alone, which was subjected to iontophoresis in the same manner.

The observed initial decline in current that appears in the plots in FIG. 2 is related to sensor wetting; the observed tapering off in the glucose plot is due to depletion of the working electrode used for reverse iontophoresis in this set of experiments.

Figure 3:
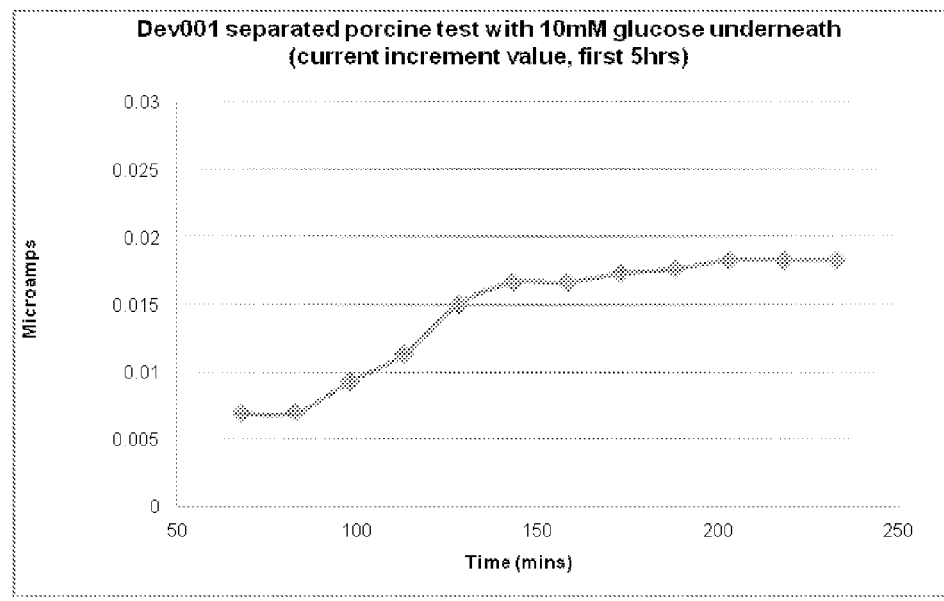
FIG. 3 is a plot of the differences between successive current measurements from plot (a) of FIG. 2.

The glucose reading at any measurement point is derived from the difference between two successive point readings, as shown in FIG. 3. The graph shows the difference between each glucose reading in FIG. 2 and the previous one, plotted against time for the first 4 hours. It was found that the cumulative build-up of the glucose concentration does not affect the sensors' ability to discern between readings, such that with different skin glucose levels, there is a discernible difference between successive measurements of concentration. The sensors retain resolution down to nanoamp (or even picoamp) levels although they are measuring currents of hundreds of nanoamps.

With reference to FIG. 3, an initial lag phase is observed while the skin is equilibrating, otherwise termed the warm-up phase. After this, the results clearly show stabilization of the glucose levels drawn during successive intervals, and the concentration at successive points is substantially constant for the given constant current applied to the skin during the reverse iontophoresis process. The experiment was carried out with full thickness (2-3 mm) porcine skin, in a lab setting without any capillary blood flow, thus the glucose was being drawn through the full thickness of the skin from the reservoir with which the lower side of the skin was placed in contact. In a live, human subject interstitial fluid would be present within the first 0.5-1 mm of the skin so the warm-up phase would be expected to be substantially shorter.

In a patch made according to the invention, the frequency or duration of iontophoresis steps could be increased during the warm-up phase in order to shorten that phase further. The detection algorithm could be programmed to recognize the end of the warm-up phase based on the substantial stabilization of the detected levels of analyte. Similarly, early in the operation of the patch the step of measuring the concentration of analyte in the sample could be repeated a number of times in quick succession (for example, 15 times) to ensure adequate wetting of the sensor to give stable readings.

An algorithm is used to determine the blood glucose level of the subject from the difference between successive measurements of concentration in the sample at each interval. The algorithm must be calibrated not only for the length of the reverse iontophoresis process but for the pre-established effectiveness of the process in extracting glucose from human subjects in general or, preferably, from the particular subject in question. For example, the algorithm may be calibrated by comparing the difference between two successive measurements of glucose concentration in the sample against an independent measurement of the glucose concentration in a finger-prick blood sample from the subject (or against the average concentration of two such finger-prick samples taken at the same times as the measurements by the patch).

Perspiration by the subject can cause a rapid increase in the rate of extraction that is not characteristic of the actual blood sugar level thus the algorithm can be made capable of detecting and eliminating such erroneous data. This would involve the software removing readings where the rise in sugar level was faster than a threshold rate 'B', where B is the maximum rate of rise of blood sugar level when taken across an average healthy and/or diabetic population after ingesting a defined amount of sugar in a liquid drink (to mimic food intake).

The algorithm may also include some compensation for a small amount of glucose that will be depleted during the operation of the sensor, although preferably in accordance with the invention this amount is very little. In some circumstances, depletion of the analyte can also continue between measurement steps as the enzymes present in the sample continue to react with it. If periods between readings are long then this becomes more significant. One solution is for the algorithm to include a further 'correction' factor allowing one to deduct a value from the difference in the readings, based on a constant that would be determined (during experimentation/clinical studies) which corresponds to some further depletion of the analyte present in the sensing region between two readings. This very much depends on the time interval between two readings, and where the time interval is only a few minutes no significant depletion of analyte is observed that would call for the correction factor/constant to be used, whereas if the time interval is say greater than 5 minutes then the extent to which the analyte depletes is proportionally higher. Another way of accounting for long lag periods between readings, is to take a 'base' reading at a given point in time at the end of the delay, followed by iontophoresis, and then to base the determination of the analyte level on the difference between the two readings taken immediately before and after the iontophoresis step.

Whilst the preferred method of extraction of analyte has been described as reverse iontophoresis, in a further embodiment of the invention the extraction process may be performed using microneedles to extract either blood samples or interstitial fluid, with or without enhancements to the extraction by integrating it with reverse iontophoresis. The microneedles may be hollow, porous, or solid. In such case the amount of analyte extracted would be substantially higher than that extracted using reverse iontophoresis alone, and hence the invention described herein would therefore have significant practical benefits, primarily in that in order to deplete entirely such large amounts of analyte between each reading may require a prohibitive amount of sensor material such as enzyme, making the sensor impractical. In the case of other types of sensors a higher resolution would be achieved when taking the difference in measurement between each extraction phase.

The invention claimed is:

1. A method of operating a device for monitoring the level of an analyte in a subject, wherein the device includes a sensor, a sensor chamber, and a microelectronic circuit, comprising the steps of:

(a) operating the microelectronic circuit to monitor the sensor to develop a measurement of the concentration of the analyte in a sample;

(b) operating the microelectronic circuit to induce a flow of a bodily fluid from the subject into the sensor chamber, thereby introducing into the sample a quantity of the analyte that is representative of the level of analyte in the subject;

(c) operating the microelectronic circuit to monitor the sensor to develop another measurement of the concentration of the analyte in the sample;

(d) operating the microelectronic circuit to determine a level of the analyte in the subject based on the difference between the measurement of concentration developed in step (c) and an immediately preceding measurement of concentration; and (e) repeating steps (b) to (d) at intervals to generate a sequence of determinations over time.

2. A method according to claim 1, wherein:
the process used to measure the concentration of analyte in the sample partially depletes the analyte in the sample.

3. A method according to claim 2, wherein the measurement in step (c) is controlled such that each measurement depletes only a small proportion of the analyte, whereby the concentration of analyte in the sample increases over successive intervals.

4. A method according to claim 2, wherein:
the microelectronic circuit is operated to allow for depletion of analyte in the sample due to the measurement process when operated to determine the level of analyte in step (d).

5. A method according to claim 2, wherein:
the microelectronic circuit is operated to allow for depletion of analyte in the sample during the intervals between successive measurements when operated to determine the level of analyte in step (d).

6. A method according to claim 2, wherein there is a rest period between each measurement step (c) and the succeeding introduction step (b);
the method further comprising a step of operating the microelectronic circuit to monitor the sensor to develop an interim measurement of the concentration of the analyte in the sample immediately before each introduction step (b), that interim measurement to be used as the immediately preceding measurement of concentration in the determination step (d).

7. A method according to claim 1, further comprising an initial step of introducing into the sample a quantity of the analyte prior to the first measurement step (a).

8. A method according to claim 7, wherein the quantity of the analyte introduced into the sample in the initial step is from a source other than the subject.

9. A method according to claim 7, wherein the initial step further comprises monitoring the sensor to carry out a set of repeated measurements of the concentration of the analyte in the sample in order to achieve stable operation of the sensor.

10. A method according to claim 1, wherein the measurement step (c) comprises taking a series of measurements and calculating an average of selected measurements in the series.

11. A method according to claim 1, wherein the determination step (d) comprises operating the microelectronic circuit to reject any measurements that give rise to a change in the determined level of analyte exceeding a threshold value.

12. A method according to claim 1, wherein the determination step (d) comprises operating the microelectronic circuit to reject any measurements before the determined level of analyte has substantially stabilized.

13. A method according to claim 1, wherein step (b) of introducing into the sample a quantity of the analyte that is representative of the level of analyte in the subject comprises performing reverse iontophoresis to extract the quantity of the analyte from interstitial fluid of the subject.

14. A method according to claim 1, wherein step (b) of introducing into the sample a quantity of the analyte that is representative of the level of analyte in the subject comprises using microneedles to extract from the subject a bodily fluid containing the quantity of the analyte.

15. A method according to claim 1, wherein the analyte is glucose.

* * * * *